(12) United States Patent
Gamble et al.

(10) Patent No.: US 6,649,362 B2
(45) Date of Patent: Nov. 18, 2003

(54) SCREENING METHOD FOR AN AGENT HAVING AN EFFECT ON A SPHINGOSINE KINASE SIGNALING PATHWAY

(75) Inventors: Jennifer Gamble, South Australia (AU); Mathew Vadas, South Australia (AU); Pu Xia, South Australia (AU); Phillip Barter, South Australia (AU); Kerry-Anne Rye, South Australia (AU); Brian Wattenberg, South Australia (AU); Stuart Pitson, South Australia (AU)

(73) Assignee: Medvet Science Pty. Ltd., Adelaide (AU)

( * ) Notice: Subject to any disclaimer, the term of this patent is extended or adjusted under 35 U.S.C. 154(b) by 0 days.

(21) Appl. No.: 09/977,217

(22) Filed: Oct. 16, 2001

(65) Prior Publication Data

US 2002/0051777 A1 May 2, 2002

Related U.S. Application Data

(63) Continuation of application No. 09/508,249, filed as application No. PCT/AU98/00730 on Sep. 8, 1998, now abandoned.

(30) Foreign Application Priority Data

Sep. 8, 1997 (AU) ............................................. PO 9002

(51) Int. Cl.[7] ................................................. C12Q 1/48
(52) U.S. Cl. ........................ 435/15; 435/69.2; 424/94.5
(58) Field of Search .................. 435/15, 69.2; 424/94.5

(56) References Cited

U.S. PATENT DOCUMENTS

| 5,780,592 A | 7/1998 | Mullner et al. | 530/359 |
| 5,928,624 A | 7/1999 | Wright et al. | 424/9.1 |

OTHER PUBLICATIONS

Ghosh T. Sphingosine 1–Phosphate . . . J of Biological Chemistry 269(36)22628–35, 1994.*
Zhang H. Sphingosine–1–Phosphate, A Novel Lipid Involved in Cellular Proliferation. J of Cell Biology 114(1)155–167, 1991.*
Tolan D. The Identification of DL–Threo Dihydrosphingosine . . . British J of Pharmacol 119(2)185–186, 1996.*
Wang F. Sphingosine 1–Phosphate Stimulates Rho Mediated Tyrosine Phosphorylation of Focal Adhesion linase and Paxillin in Swiss 3T3 Fibroblasts. Biochem J 324, 481–8, 1997.*
Wang et al., "Sphingosine 1–phosphate stimulates Rho–mediated tyrosine phosphorylation of focal adhesion kinase and paxillin in Swiss 3T3 fibroblasts," *Biochem. J.* (1997), vol. 324, pp. 481–488, Great Britain.

* cited by examiner

*Primary Examiner*—Ralph Gitomer
(74) *Attorney, Agent, or Firm*—Foley & Lardner

(57) ABSTRACT

A screening method for identifying a therapeutic candidate for a coronary heart disease or an inflammatory condition is disclosed. The screening method tests for the presence or absence of an effect by a putative therapeutic agent on a component of a sphingosine kinase signaling pathway.

8 Claims, 10 Drawing Sheets

A.

B.

SCREENING METHOD FOR AN AGENT HAVING AN EFFECT ON A SPHINGOSINE KINASE SIGNALING PATHWAY

This is a Continuation Application of application Ser. No. 09/508,249, filed Jun. 01, 2000, now abandoned which claims priority to Australia PO 9002 filed Sep. 8, 1997 which is in turn a PCT National Stage No. PCT/AU/98/00730, filed Sep. 8, 1998.

FIELD OF THE INVENTION

The present invention relates generally to a method of modulating cellular activity and agents useful for same. More particularly, the present invention contemplates a method of modulating endothelial cell activity and even more particularly endothelial cell adhesion molecule expression. Most particularly, the present invention provides a method of treating coronary heart disease by preventing or reducing endothelial cell adhesion molecule expression.

BACKGROUND OF THE INVENTION

Bibliographic details of the publications referred to by author in this specification are collected at the end of the description. Sequence Identity Numbers (SEQ ID NOs.) for the nucleotide and amino acid sequences referred to in the specification are defined immediately before the bibliography.

Atherosclerotic coronary heart disease is one of the major causes of death in the western world (World Health Statistics Annual). An earlier event in atherogenesis is the adhesion of monocytes to the endothelium via adhesion molecules such as VCAM-1, ICAM-1 and E-selectin, all of which are rapidly synthesised in response to cytokines. VCAM-1 is primarily involved in the adhesion of mononuclear leukocytes to the endothelium. It is rapidly induced by the inflammatory cytokines IL-1 and TNF-$\alpha$, and its induction is sustained for 49 to 72 hours. ICAM-1 is expressed on many cells types and is involved in both monocyte and lymphocyte adhesion to activated endothelium. E-selectin is an endothelial specific adhesion molecule important in capturing leukocytes from the axial stream to roll along the endatheliurn (Abbassi et al., 1993).

There is considerable evidence for the involvement of adhesion molecules in the development of early atherosclerotic lesions and in mature atherosclerotic plaques (Van der Wal et al., 1992). Variable and low levels of E-selectin and VCAM-1 have been detected in the arterial endothelium over plaques (Van der Wal et al., 1992; Wood et al., 1993). VCAM-1 has also been observed in areas of neovasculatization and in inflammatory infiltrates at the base of plaques, suggesting that intimal neovascularization may be an important site of inflammatory cell recruitment into advanced coronary lesions (O'Brien et al., 1993). ICAM-1 has been shown to be expressed on the endothelium overlaying atheromatous plaques (Johnson-Tidey et al., 1994).

The signals that lead to upregulation of cellular activities such as expression of adhesion molecules have not been defined. Elucidating these cellular signalling mechanisms is necessary for the development of therapeutic strategies to disease conditions in which said cellular activities are harmful such as coronary heart disease and inflammatory conditions.

In work leading up to the present invention, the inventors have identified a sphingosine kinase signalling pathway via which cellular activities such as adhesion molecule expression are achieved. By regulating the expression and activity of individual components of this pathway, these cellular activities can be modulated. The inventors have also developed a rapid, high volume assay for detecting agents exhibiting sphingosine kinase activity and agents which can act as agonists and antagonists of sphingosine kinase activity.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

One aspect of the present invention relates to a method of modulating cellular activity in a mammal said method comprising administering to said mammal an effective amount of an agent for a time and under conditions sufficient to modulate the activity of one or more components of a sphingosine kinase signalling pathway.

Another aspect of the present invention provides a method of modulating adhesion molecule expression in a mammal said method comprising administering to said mammal an effective amount of an agent for a time and under conditions sufficient to modulate the activity of one or more components of a sphingosine kinase signalling pathway.

Yet another aspect of the present invention provides a method of modulating adhesion molecule expression in a mammal said method comprising administering to said mammal an effective amount of an agent for a time and under conditions sufficient to modulate the activity of one or both of sphingosine kinase and/or Sph-1-P.

Still another aspect of the present invention relates to a method of modulating endothelial cell adhesion molecule expression in a mammal said method comprising administering to said mammal an effective amount of an agent for a time and under conditions sufficient to modulate the activity of one or more components of a sphingosine kinase signalling pathway.

Still yet another aspect of the present invention provides a method of downregulating endothelial cell adhesion molecule expression in a mammal said method comprising administering to said mammal an effective amount of an agent for a time and under conditions sufficient to downregulate the activity of one or both of sphingosine kinase and/or Sph-1-P.

A further aspect of the present invention relates to a method of modulating adhesion molecule expression in a mammal said method comprising administering to said mammal an effective amount of one or more components of a sphingosine kinase signalling pathway or functional equivalents thereof.

Another further aspect of the present invention relates to a method of treatment or prophylaxis of a disease condition involving inflammatory mechanisms said method comprising administering to said mammal an effective amount of an agent for a time and under conditions sufficient to modulate the activity of one or more components of a sphingosine kinase signalling pathway wherein said modulation results in modulation of adhesion molecule expression.

Still another further aspect of the present invention provides a method of treating a mammal exhibiting coronary heart disease said method comprising administering to said mammal an effective amount of an agent for a time and under conditions sufficient to downregulate the activity of one or more components of a sphingosine kinase signalling pathway wherein said downregulation results in downregulation of endothelial cell adhesion molecule expression.

Still yet another further aspect of the present invention provides a method of treatment or prophylaxis of a disease condition involving inflammatory mechanisms said method comprising administering an effective amount of one or more components of a sphingosine kinase signalling pathway or functional equivalents thereof to said mammal.

In still yet another further aspect the present invention relates to the use of an agent capable of modulating the activity of one or more components of a sphingosine kinase signalling pathway in the manufacture of a medicament for the modulation of adhesion molecule expression in a mammal.

Another aspect of the present invention relates to the use of one or more components of a sphingosine kinase signalling pathway or functional equivalents thereof in the manufacture of a medicament for the modulation of adhesion molecule expression in a mammal.

Yet another aspect of the present invention relates to agents for use in modulating one or more components of a sphingosine kinase signalling pathway wherein modulating said components modulates adhesion molecule expression.

Yet another aspect of the present invention relates to one or more components of a sphingosine kinase signalling pathway or functional equivalents thereof for use in modulating adhesion molecule expression in a mammal.

Still another aspect of the present invention relates to a pharmaceutical composition comprising an agent capable of modulating one or more components of a sphingosine kinase signalling pathway wherein said modulation results in modulation of adhesion molecule expression, together with one or more pharmaceutically acceptable carriers and/or diluents.

Still yet another further aspect of the present invention relates to a pharmaceutical composition comprising one or more components of a sphingosine kinase signalling pathway or functional equivalents thereof together with one or more pharmaceutically acceptable carriers and/or diluents.

A further aspect of the present invention provides a method of detecting an analyte structurally or functionally reactive with a lipid, said method comprising the steps of contacting either:

(i) said analyte which analyte is radio labelled; or (ii) said analyte and a reporter molecule which reporter molecule is radio labelled, said analyte being contacted with said lipid simultaneously with or separately to said reporter molecule;

with said lipid in the presence of a scintillant for a time and under conditions sufficient for a lipid-radio label complex to form and to excite said scintillant, and detecting said excited scintillant.

Another further aspect of the present invention relates to a method of detecting an analyte structurally or functionally reactive with sphingosine, said method comprising the steps of contacting either:

(i) said analyte which analyte is radio labelled; or (ix) said analytic and a reporter molecule which reporter molecule is radio labelled, said analyte being contacted with said sphingosine simultaneously with or separately to said reporter molecule;

with said lipid in the presence of a scintillant for a time and under conditions sufficient for a sphingosine-radio label complex to form and to excite said scintillant, and detecting said excited scintillant.

Still another further aspect of the present invention provides a method for detecting an analyte exhibiting sphingosine kinase activity, said method comprising the steps of contacting said analyte and $^{33}$JP-ATP with sphingonsine in the presence of a scintillant, said analyte being contacted with said sphingosine simultaneously with or separately to said $^{33}$P-ATP, for a time and under conditions sufficient for $^{33}$P-sphingosine complex to form and to excite said scintillant, and detecting said excited scintillant.

BRIEF DESCRIPTION OF THE DRAWINGS

FIG. 2A filled symbols show the effect of the cell-permeable ceramide (C2-ceramide) on adhesion proteins. The open symbols show the effect of ceramide in the presence of 100U/ml TNF. In FIG. 2B the effect of sphingosine-1-phosphate (Sph-1-P) is shown. FIG. 2C shows the effect dimethylsphingosine (DMS) on adhesion protein expression (MFI) stimulated by TNF or Sph-1-P. In FIG. 2D the effect of these agents on E-selectin mRNA is shown.

FIG. 4B top shows gel retardations with NF-κB. FIG. 4B bottom shows supershifts with antibodies specific for p50 and p65 components of NIF-κB and demonstrates the similar composition of NF-κB stimulated by TNF and Sph-1-P.

DETAILED DESCRIPTION OF THE PREFERRED EMBODIMENTS

Figure 1:
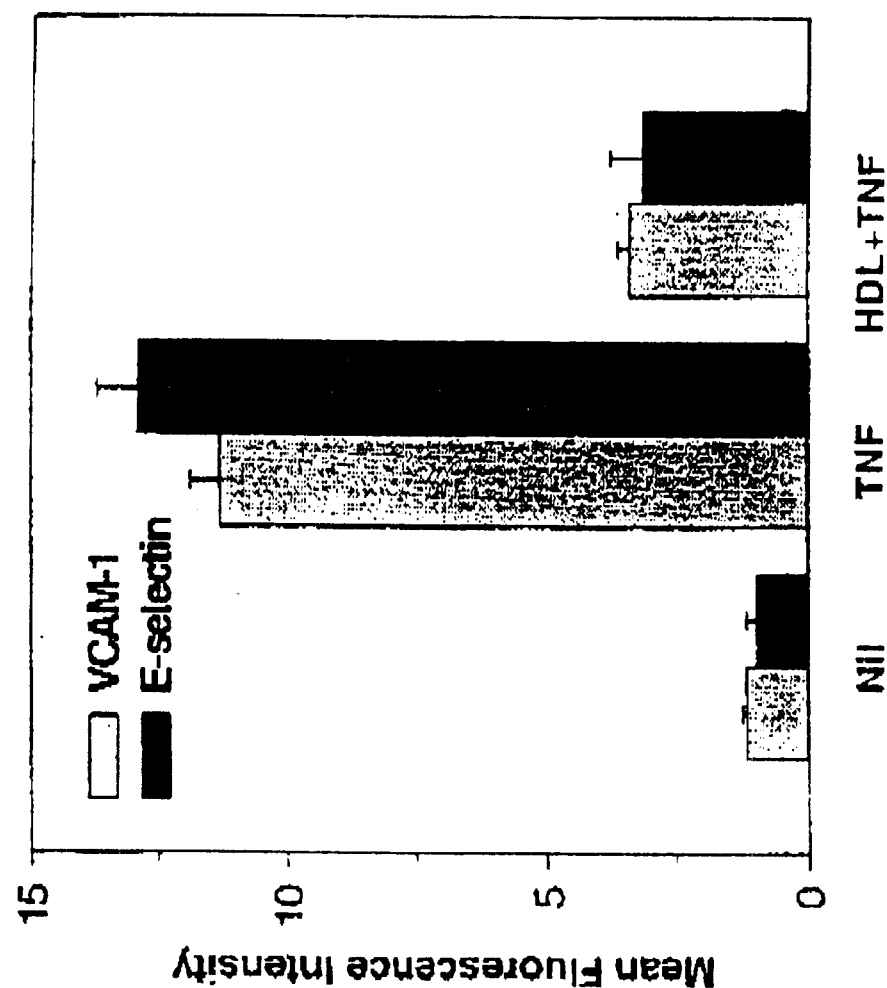
FIG. 1 is a graphical representation of the effect of high density lipoprotein (HDL) on tumour necrosis factor (TNF) mediated induction of adhesion proteins VCAM-1 and E-selectin. Mean fluorscence intensity is a flow cytometric measurement signifying the intensity of expression of adhesion molecules on the cell surface.

Accordingly, one aspect of the present invention relates to a method of modulating cellular activity in a mammal said method comprising administering to said mammal an effective amount of an agent for a time and under conditions sufficient to modulate the activity of one or more components of a sphingosine kinase signaling pathway.

The term "mammal" includes humans, primates, livestock animals (e.g. horses, cattle, sheep, pigs, donkeys), laboratory test animals (e.g. mice, rats, rabbits, guinea pigs), companion animals (e.g. dogs and cats) and captive wild animals (e.g. kangaroos, deer, foxes). Preferably, the mammal is a human or a laboratory test animal. Even more preferably the mammal is a human.

Reference to "modulating cellular activity" is a reference to up-regulating, down-regulating or otherwise altering any one or more of the activities which a cell is capable of performing such as, but not limited to, one or more of chemokine production, cytokine production, nitric oxide synthesase production, adhesion molecule expression and production of other inflammatory modulators. Preferably said cellular activity is adhesion molecule expression. Reference hereinafter to adhesion molecule expression should be read as including reference to other cellular activities.

Accordingly, there is provided a method of modulating adhesion molecule expression in a mammal said method comprising administering to said mammal an effective amount of an agent for a time and under conditions sufficient to modulate the activity of one or more components of a sphingosine kinase signalling pathway.

The term "expression" refers to the transcription and translation of a nucleic acid molecule resulting in the synthesis of a polypeptide.

Reference to "adhesion molecule" should be understood as a reference to a molecule which mediates the binding of a cell to another cell or to a protein such as an extracellular matrix protein. Examples of adhesion molecules include, but are not limited to, integrins, selectins (e.g. E-selectin, P-selectin), members of the immunoglobulin-gene superfamily (e.g. VCAM-1, ICAM-1) and CD44.

Reference to modulating the "activity" of sphingosine kinase signalling pathway components is a reference to modulating the functions which said components are capable of performing such as but not limited to increasing or decreasing the role or extent to which a given component performs its function or modifying the nature of the function which a given component performs. Modulating said "activity" should also be understood to encompass increasing or decreasing the concentration levels of a given component. Modulation of said "activity" may be achieved by:

(i) modulation of the catalytic activity of sphingosine kinase by competition with substrate (for example, sphingosine or ATP), (ii) interference with the catalytic activity of sphingosine kinase by an allosteric mechanisms (binding to sites on the molecule other than the substrate-binding sites); or (iii) interfering with enzyme activation, such as by altering:

post-translational covalent modification such as phosphorylation, lipid modification
non-covalent coupling to a required co-activator such as a protein, lipid or ion
subcellular localisation of the enzyme.

A "sphingosine kinase signalling pathway" is defined as a signalling pathway which utilises one or both of sphingosine kinase and/or sphingosine-1-phosphate. Without limiting the present invention to any one theory or mode of action, it is thought a sphingosine kinase signalling pathway cascade which results in adhesion molecule expression may take the form of:

(i) the generation of ceramide from sphingomyelin via S. Mase activity, said ceramide being converted to sphingosine;

(ii) sphingosine-1-phosphate (referred to hereinafter as "Sph-1-P") generation by stimulation of sphingosine kinase; and (iii) the activation of MEK/ERK and nuclear translocation of NF-κB downstream from Sph-1-P generation, said downstream events leading to adhesion molecule expression.

Accordingly, the term "components" should be understood to refer to any molecule which is or may be involved in a sphingosine kinase signalling pathway cascade and includes, but is not limited to, cellular proteins, metabolites (e.g. sphingomyelin, ceramide, sphingosine and Sph-1-P), kinases (e.g. S. Mase, sphingosine kinase, protein kinase C and ERK) and transcription factors (e.g. NF-κB). Preferably, said components are sphingosine kinase and/or Sph-1-P.

According to this preferred embodiment there is provided a method of modulating adhesion molecule expression in a mammal said method comprising administering to said mammal an effective amount of an agent for a time and under conditions sufficient to modulate the activity of one or both of sphingosine kinase and/or Sph-1-P.

A key event in many disease conditions is the upregulation of cellular activities such as those which lead to inflammation. For example, upregulation of the production of inflammatory mediators such as cytokines, chemokines, eNOS and upregulation of adhesion molecule expression. Said upregulation may be induced by a number of stimuli including, for example, inflammatory cytokines such as tumour necrosis factor-α (TNF-α) and interleukin-1 (IL-1) endotoxin, oxidised or modified lipids, radiation or tissue injury. In a preferred aspect said cellular activity is endothelial cell activity.

Accordingly, the present invention relates to a method of modulating endothelial cell adhesion molecule expression in a mammal said method comprising administering to said mammal an effective amount of an agent for a time and under conditions sufficient to modulate the activity of one or more components of a sphingosine kinase signalling pathway.

Most preferably said components are sphingosine kinase and/or Sph-1-P.

While most of the components involved in a sphingosine kinase signalling pathway are stimulatory for a given cellular activity, inhibitory signalling components are also evident. For example, Sph-1-P is generated from sphingosine by sphingosine kinase. Stimulation of endothelial cells causes a rapid and transient increase in cytosolic sphingosine kinase activity which leads to upregulation of adhesion molecule expression. The production of Sph-1-P is induced in parallel with sphingosine kinase activity. However, inhibitory components of a sphingosine kinase signalling pathway result in inhibition of adhesion molecule expression. Accordingly, the term "modulate" in relation to the activity of any one or more components of the sphingosine kinase signalling pathway refers to upregulating or downregulating or otherwise altering said activity. The preferred method is to downregulate sphingosine kinase pathway activity either by inhibiting or reducing the activity of one or more stimulatory components of a sphingosine kinase signalling pathway or by upregulating the activity of one or more inhibitory components of said pathway. However, modulation of the activity of said components wherein adhesion molecule expression is upregulated may be desired under certain circumstances. Most preferably, the biological activity of said stimulatory components is down-regulated.

According to this most preferred embodiment, there is provided a method of downregulating endothelial cell adhesion molecule expression in a mammal said method comprising administering to said mammal an effective amount of an agent for a time and under conditions sufficient to downregulate the activity of one or both of sphingosine kinase and/or Sph-1-P.

Modulation of said activity by the administration of an agent to a mammal can be achieved by one of several techniques, including but in no way limited to introducing into said mammal a proteinaceous or non-proteinaceous molecule which:

(i) modulates synthesis of said components, (ii) functions as an antagonist to said component, (iii) functions as an agonist to said component.

Said proteinaceous molecule may be derived from natural, recombinant or synthetic sources including fusion proteins or following, for example, natural product screening. Said non-proteinaceous molecule may be derived from natural sources, such as for example natural product screening or may be chemically synthesised. The present invention contemplates chemical analogs of said components capable of acting as agonists or antagonists of said components. Chemical agonists may not necessarily be derived from said components but may share certain conformational similarities. Alternatively, chemical agonists may be specifically designed to mimic certain physiochemical properties of said components. Antagonists may be any compound capable of blocking, inhibiting or otherwise preventing said components from carrying out their normal biological functions. Antagonists include monoclonal antibodies specific for said components, or parts of said components, and antisense nucleic acids which prevent transcription or translation of genes or mRNA in mammalian cells.

The method of the present invention is exemplified herein utilising high density lipoprotein (referred to herein as "HDL"). Treatment of endothelial cells with HDL inhibits both the amplitude and duration of TNF-α induced sphingosine kinase activation. HDL treatment substantially blunts the amplitude and duration of Sph-1-P formation by inhibiting sphingosine kinase activity. The inhibition of Sph-1-P formation results in blunting of downstream pathway events including blunting of MEK/ERK activation and NF-κB nuclear translocation thereby reducing adhesion protein expression. Similarly, N,N-dimethyl sphingosine decreases TNF-α induced adhesion protein expression and mRNA levels by competitively inhibiting sphingosine kinase activity. Interruption of the sphingosine kinase signalling pathway at this point prevents the downstream formation of intracellular Sph-1-P thereby preventing the further downstream events of MEK/ERK and NF-κB stimulation which lead to adhesion protein expression.

In a most preferred embodiment the present invention relates to a method of downregulating endothelial cell adhesion molecule expression in a mammal said method comprising administering to said mammal an effective amount of HDL for a time and under conditions sufficient to downregulate sphingosine kinase activity.

An "effective amount" means an amount necessary to at least partly obtain the desired response or to delay the onset or inhibit progression or halt altogether the onset or progression of adhesion molecule expression. This amount varies depending upon the health and physical condition of the individual to be treated, the taxonomic group of the individual to be treated, the assessment of the medical situation and other relevant factors. It is expected that the amount will fall in a relatively broad range that can be determined through routine trials.

Modulation of cellular adhesion molecule expression can also be achieved by the administration of one or more sphingosine kinase signalling pathway components or functional equivalents thereof.

Accordingly, another aspect of the present invention relates to a method of modulating adhesion molecule expression in a mammal said method comprising administering to said mammal an effective amount of one or more components of a sphingosine kinase signalling pathway or functional equivalents thereof.

The term "functional equivalents" used herein includes but is not limited to derivatives having the functional activity of said components.

Derivatives include fragments, parts, portions, chemical equivalents, mutants, homologs, mimetics from natural, synthetic or recombinant sources including fusion proteins. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence. Substitutional amino acid variants are those in which at least one residue in the sequence has been removed and a different residue inserted in its place. Additions to amino acid sequences including fusions with other peptides, polypeptides or proteins.

The derivatives of said components include fragments having particular epitopes or parts of the entire component fused to peptides, polypeptides or other proteinaceous or non-proteinaceous molecules. For example, said components or derivative thereof may be fused to a molecule to facilitate its entry into a cell. Analogs of said components contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogs. Derivatives of nucleic acid sequences may similarly be derived from single or multiple nucleotide substitutions, deletions and/or additions including fusion with other nucleic acid molecules.

The derivatives of the nucleic acid molecules of the present invention include oligonucleotides, PCR primers, antisense molecules, molecules suitable for use in cosuppression and fusion of nucleic acid molecules.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials: carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, omithine, sarcosine, 4-amino-3-hydroxy-6-methylheptanoic acid, 2-thienyl alanine and/or D-isomers of amino acids. A list or unnatural amino acid contemplated herein is shown in Table 1.

TABLE 1

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgtn |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |

TABLE 1-continued

| Non-conventional amino acid | Code | Non-conventional amino acid | Code |
|---|---|---|---|
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2.2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-metylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2.2-diphenylethyl) carbamylmethyl)glycine | Nnbhm | N-(N-(3.3-diphenylpropyl) carbamylmethyl)glycine | Nnbhe |
| 1-carboxy-1-(2.2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_K$ and N-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

The present invention is useful in relation to human disease conditions For example the present invention is particularly useful, but in no way limited to, use as a prophylactic or as a therapy in relation to disease conditions which involve inflammatory mechanisms, such as coronary heart disease.

Accordingly, another aspect of the present invention relates to a method of treatment or prophylaxis of a disease condition involving inflammatory mechanisms in a mammal said method comprising administering to said mammal an effective amount of an agent for a time and under conditions sufficient to modulate the activity of one or more components of a sphingosine kinase signalling pathway wherein said modulation results in modulation of adhesion molecule expression.

Preferably modulation of said adhesion molecule expression is modulation of endothelial cell adhesion molecule expression.

Even more preferably, said components are sphingosine kinase and/or Sph-1-P. Most preferably said components are downregulated said downregulation resulting in downregulation of adhesion molecule expression.

In a most preferred embodiment there is provided the method of treating a mammal exhibiting coronary heart disease said method comprising administering to said mammal an effective amount of an agent for a time and under conditions sufficient to downregulate the activity of one or more components of a sphingosine kinase signalling pathway wherein said downregulation results in downregulation of endothelial cell adhesion molecule expression.

Most preferably said components are sphingosine kinase and/or Sph-1-P

Another aspect of the present invention provides a method of treatment or prophylaxis of a disease condition involving inflammatory mechanisms in a mammal said method comprising administering to said mammal an effective amount of one or more components of a sphingosine kinase signalling pathway or functional equivalents thereof wherein said modulation results in modulation of adhesion molecule expression.

Administration of the agent or component or functional equivalent thereof, in the form of a pharmaceutical composition, may be performed by any convenient means. The agent or component or functional equivalent thereof of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.1 mg to about 1 mg of the agent or component or functional equivalent thereof may be administered per kilogram of body weight per day. Dosage regimes may be adjusted to provide the optimum therapeutic response. For example, several divided doses may be administered daily, weekly, monthly or at other suitable time intervals or the dose may be proportionally reduced as indicated by the exigencies of the situation. The agent or component or functional equivalent thereof may be administered in a convenient manner such as by the oral, intravenous (where water soluble), intraperitoneal, intramuscular, subcutaneous, intradermal or suppository routes or implanting (e.g. using slow release molecules). With particular reference to use of the agent or component or functional equivalent thereof, said agent or component or functional equivalent thereof may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In a preferred embodiment of the present invention, the agent used in the method is linked to an antibody specific for coronary endothelial cells to enable specific delivery of said agent to these cells.

In yet another aspect the present invention relates to the use of an agent capable of modulating the activity of one or more components of a sphingonsine kinase signalling pathway in the manufacture of a medicament for the modulation of adhesion molecule expression in a mammal.

Preferably modulation of said adhesion molecule expression is modulation of endothelial cell adhesion molecule expression.

Even more preferably, said components are sphingosine kinase and/or Sph-1-P Most preferably said components are downregulated said downregulation resulting in downregulation of adhesion molecule expression.

Another aspect of the present invention relates to the use of one or more components of a sphingosine kinase signalling pathway or functional equivalents thereof in the manufacture of a medicament for the modulation of adhesion molecule expression in a mammal.

Yet another aspect of the present invention relates to agents for use in modulating one or more components of a sphingosine kinase signalling pathway wherein modulating said components modulates adhesion molecule expression.

Preferably modulation of said adhesion molecule expression is modulation of endothelial cell adhesion molecule expression.

Even more preferably, said components are sphingosine kinase and/or Sph-1-P. Most preferably said components are downregulated said downregulation resulting in downregulation of adhesion molecule expression.

A further aspect of the present invention relates to one or more components of a sphingosine kinase signalling pathway or functional equivalents thereof for use in modulating adhesion molecule expression in a mammal.

Yet another further aspect of the present invention relates to a pharmaceutical composition comprising an agent capable of modulating one or more components of a sphingosine kinase signalling pathway wherein said modulation results in modulation of adhesion molecule expression, together with one or more pharmaceutically acceptable carriers and/or diluents.

In another further aspect, the present invention relates to a pharmaceutical composition comprising one or more components of a sphingosine kinase signalling pathway or functional equivalents thereof together with one or more pharmaceutically acceptable carriers and/or diluents.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 $\mu$g and 2000 mg of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule capable of modulating the expression of a component of the sphingosine kinase signalling pathway. The vector may, for example, be a viral vector.

To facilitate the identification of agents suitable for use in the method of present invention, the inventors have developed a rapid, facile, high volume assay for screening for agents which are either structurally or functionally reactive with a lipid. In the context of identifying agents for use in the method of the present invention, this assay provides a means of easily and rapidly identifying agents which either mimic the activity of a component of sphingosine kinase signalling pathway or act as an agonist or antagonist to a component of sphingosine kinase signalling pathway.

Accordingly, another aspect of the present invention provides a method of detecting an analyte structurally or functionally reactive with a lipid, said method comprising the steps of contacting either:

(i) said analyte, which analyte is radio labelled; or
(ii) said analyte and a reporter molecule which reporter molecule is radio labelled, said analyte being contacted simultaneously with or separately to said reporter molecule;

with said lipid in the presence of a scintillant for a time and under conditions sufficient for a lipid-radio label complex to form and to excite said scintillant, and detecting said excited scintillant.

Preferably said analyte or analyze and reporter molecule are contacted with lipid and scintillant coupled to a solid support.

Reference to "lipid" should be understood as a reference to any molecule comprising a lipid component. Preferably said lipid is a lipid component of the sphingosine kinase signalling pathway and even more preferably sphingosine. This aspect of the present invention is exemplified herein with respect to sphingosine, however this should not be understood as imposing any limitation on the application of this method.

Accordingly, the present invention more particularly provides a method of detecting an analyte structurally or functionally reactive with sphingosine, said method comprising the steps of contacting either:

(i) said analyte which analyte is radio labelled; or
(ii) said analyte and a reporter molecule which reporter molecule is radio labelled, said analyte being contacted simultaneously with or separately to said reporter molecule;

with said sphingosine in the presence of a scintillant for a time and under conditions sufficient for a sphingosine-radio label complex to form and to excite said scintillant, and detecting said excited scintillant.

Preferably, said analyte or analyte and reporter molecule are contacted with sphingosine and scintillant which sphingosine may be coupled to a solid support having a scintillant already coupled thereto using a method as described in Example 9.

Reference to an analyte which is "structurally" reactive with a lipid should be understood as a reference to a molecule which either binds, links or otherwise associates with said lipid. Said association may be due to the formation of a peptide bond, ionic bond, hydrogen bond or other interactive bonding mechanisms. Reference to an analyte which is "functionally" reactive with a lipid should be understood as a molecule which, when it interacts with said lipid, directly or indirectly causes a functional process to take place. A functionally reactive analyte may or may not also structurally interact with said lipid. An example of a functionally reactive analyte is an enzyme (for example, a sphingosine kinase equivalent) the substrate of which is a lipid (for example, sphingosine). In accordance with this example, an enzyme exhibiting sphingosine kinase activity is functionally reactive in that it will phosphorylate sphingosine in the presence of ATP. The occurrence of the structural or functional activity is detected by the method of this aspect of the present invention.

The detection of functional or structural reactivity is based on the formation, by the lipid, of a radio labelled complex. Due to the proximity of the complexed radio label with the scintillant, the scintillant becomes excited.

The analyte which is being assayed may be directly radio labelled. This is useful where, for example, said analyte directly associates with said lipids. Alternatively, a reporter molecule may be radio labelled. Reference to "reporter molecule" should be understood as a reference to any molecule, other than the analyte, which detects reactivity between the analyte and lipid. For example, the reporter molecule may be an antibody which recognises one or more epitopes present on the surface of the analyte of interest. This method of detection is an indirect method of detection, commonly referred to as a "sandwich assay". Alternatively, the reporter molecule may be a molecule required to both facilitate reactivity between the analyte and the lipid, for example the reporter molecule may be a substrate, in addition to facilitating detection. In the method exemplified herein, the reporter molecule is $^{33}$P-ATP. An analyte exhibiting sphingosine kinase activity will phosphorylate sphingosine in the presence of $^{33}$P-ATP resulting in the coupling of $^{33}$P to the sphingosine. In the absence of a phosphate reporter molecule, the analyte would be unable to phosphorylate the lipid. Further, since the analyte does not structurally interact with the lipid sufficiently to facilitate detection, the method of detection of the functional reactivity is based on the phosphorylation of the lipid with radio labelled phosphate.

It should be understood, that even where the analyte is radio labelled and said analyte binds to the lipid, it may nevertheless be necessary that a molecule other than the analyte is present in the reaction mixture to facilitate reactivity of the analyte with the lipid.

Solid supports suitable for use in the present invention include, but are not limited to, micro-titre plates, 96 well plates, columns and micro-beads.

Preferably, the present invention provides a method for detecting an analyte exhibiting sphingosine kinase activity, said method comprising the steps of contacting said analyte and $^{33}$P-ATP with sphingosine in the presence of a scintillant, said analyte being contacted with said sphingosine simultaneously with or separately to said $^{33}$P-ATP, for a time and under conditions sufficient for $^{33}$P-sphingosine complex to form and to excite said scintillant, and detecting said excited scintillate.

Preferably said analyte and $^{33}$P-ATP are contacted with sphingosine and scintillant coupled to a solid support.

Detection of the excited scintillant may be by any suitable means including, but not limited to, a scintillation counter.

The analyte which is assayed in the method of this aspect of the present invention may be in any suitable form. A fluid form is particularly useful as are tissue extracts such as lysates or homogenates. Said analyte may be a proteinaceous or a non-proteinaceous molecule derived from natural, recombinant or synthetic sources.

In another aspect, the method of the present invention should be understood to extend to the detection of agents which act as agonists or antagonists of analytes which either structurally or functionally react with a lipid. For example, the present invention is particularly useful for detecting agonists or antagonists of sphingosine kinase activity. This may be achieved, in accordance with this embodiment of the present invention, by contacting the sphingosine with sphingosine kinase in the presence of the potential agonistic or antagonistic agent. Comparison of the degree of sphingosine-radio label complex formation relative to a control assay in which addition of said agent was omitted is indicative of agonistic or antagonistic agent activity. Specifically, an increase in sphingosine $^{33}$P complex formation relative to the control is indicative of agonistic activity while a decrease in sphingosine $^{33}$P complex activity is indicative of antagonistic activity. This aspect of the present invention should not in any way be taken as limited to the embodiment described above. Rather this aspect of the present invention can be applied to detect antagonists or agonists of any analyte which either structurally or functionally react with a lipid.

Agents suitable for testing in method of the present invention include, but are not limited to compounds isolated from chemical libraries or broths produced from fermentation of an organisms.

With respect to the preferred embodiment detailed above, sources of sphingosine kinase suitable for use in the method of this aspect of the present invention include, but are not limited to: (i) partially purified sphingosine kinase derived from mammalian issue. (ii) crude homogenates of mammalian tissue exhibiting enzyme activity, (iii) recombinant enzyme or (iv) HUVEC crude lysate.

Further features of the present invention are more fully described in the following examples. It is to be understood, however, that this detailed description is included solely for the purposes of exemplifying the present invention. It should not be understood in any way as a restriction on the broad description of the invention as set out above.

EXAMPLE 1

HDL Isolation

HDL were isolated from normal healthy adult donors by sequential ultracentrifugation in the density range of 1.07–1.21 g/ml. Resulting preparation of HDL contained two main populations: one with particles of Stokes' diameter 10.45 nm ($HDL_2$) and one with particles of diameter 8.6 nm ($HDL_3$). Since the inhibition of adhesion molecules expression of $HDL_3$ was stronger than that induced by other native or reconstituted HDL particles from purified Apo-A-1 and egg phosphatidylcholin or sphingomyelin, $HDL_3$ was thus used in this study. In the examples we have used the human HDL, subfraction (d=1.13–1.21 g/ml) in order to minimise possible confounding effects of variations in the relative proportions of $HDL_2$ and $HDL_3$ in the plasma of different subjects. As shown in FIG. 1 $HRL_3$ inhibited the TNFα-induced expression of VCAM-1 and E-selectin by human umbilical vein endothelial cells (HUVECs) by >80%.

EXAMPLE 2

Sphingosine Kinase Signalling Pathway Methodology

Effect of HDL on TNFα-Induced Adhesion Protein Expression by HUVECs

Confluent monolayers of HUVECs were preincubated with or without HDL that was isolated as the fraction of density 1.13–1.21 g/ml from human plasma at a concentration of 1 mg/ml of apoA-1. After 16-h preincubation, the cells were treated with TNFα (100 U/ml). Following 4-h treatment of TNFα, the cell-surface expression of VCAM-1 and E-selectin was measured by using flow cytometry.

Effect of Ceramide and Sph-1-P an Adhesion Protein Expression

HUVECs were treated with an increasing concentration of $C_2$-ceramide with or without TNF 30 α(100 U/ml), or an increasing concentration of Sph-1-P for 4 h. The cell-surface expression of VCAM-1 or E-selectin was measured by flow cytometry. Effect of sphingosine kinase inhibitor (DMS) on the expression of VCAM-1 and E-selectin. The cells were treated with a vehicle (Ni1), DMS (5 $\mu$M). Sph-1-P (5 $\mu$M), $C_2$-ceramide (10 $\mu$M) or TNFα (100 U/ml) for 4 h, then measure VCAM-1 or E-selectin expression. Effect of agents on E-selectin mRNA levels and the comparison between the effect of HDL and DMS. After the indicated treatment for 4 h. E-selectin mRNA levels were measured by Northern blotting assay. Results shown in (D) are representative of three similar experiments.

Effect of HDL on TNF α-Induced Sphingomyelin Hydrolysis, Ceramide Generation, Sphingosine Kinase Activation, and Sph-1-P Production HUVECs were labelled with [$^1$H]sphingomyelin was measured at the desired time point of TNFα treatment. The unlabelled cells were treated with HDL and/or TNFα as indicated, cells were lysed to measure ceramide levels and sphingosine kinase activity, respectively. The cells were permeabilized to measure the production of Sph-1-P in vivo.

Effect of HDL and Sphingosine Kinase Pathway on ERK and NFκB Activation

After the cells were treated with an agent for 30 min. ERK activities were assayed with myeline basic protein (MBP) as substrate after immunoprecipitation with antibodies against p42/p44$^{MAPK}$ (Berra et al., 1995: Li et al., 1996; Lee et al., 1997). The kinase reaction products were separated on 10% SDS-polyacrylamide gels. Bar graph depicting ERK activities were quantified by Phosphoimager. NF-κB binding activity was measured by electrophoretic mobility shift assay after 30 min treatment as indicated. The specific NF-κB binding complexes were identified by the super-shift gel assay with anti-p50 and anti-p65 antibodies and by competition analyses with the addition of a 50-fold molar excess of unlabelled NF-κB oligonucleotides.

EXAMPLE 3

Sphingosine Kinase Signalling Pathway

Figure 2:
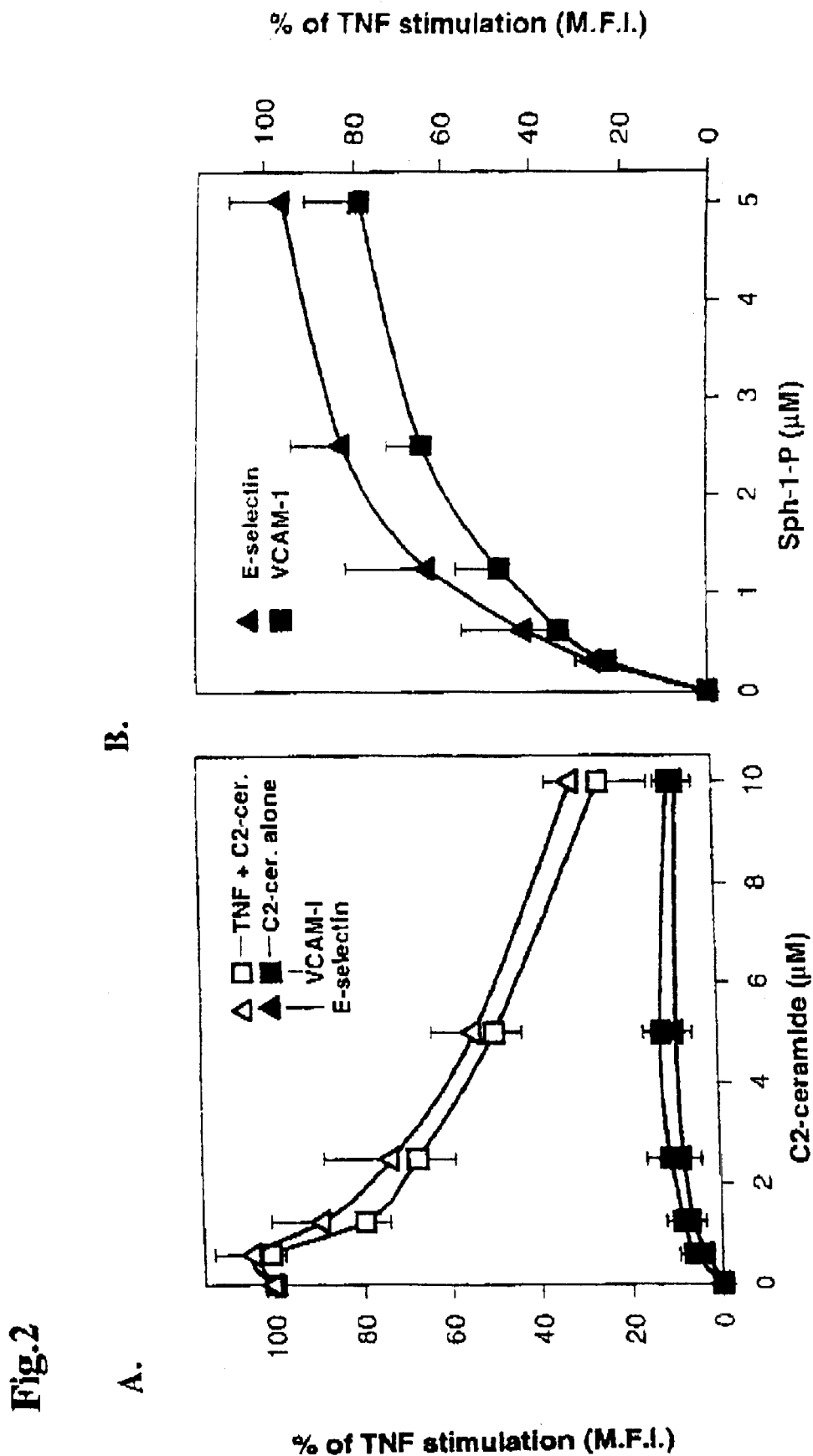
FIG. 2 is a graphical representation of the effect of sphingosine kinase inhibitor on adhesion protein expresssion. Intensity of cell surface expression was measured as a percent of the mean fluorescence intensity stimulated by 100U of TNF.
Figure 2:
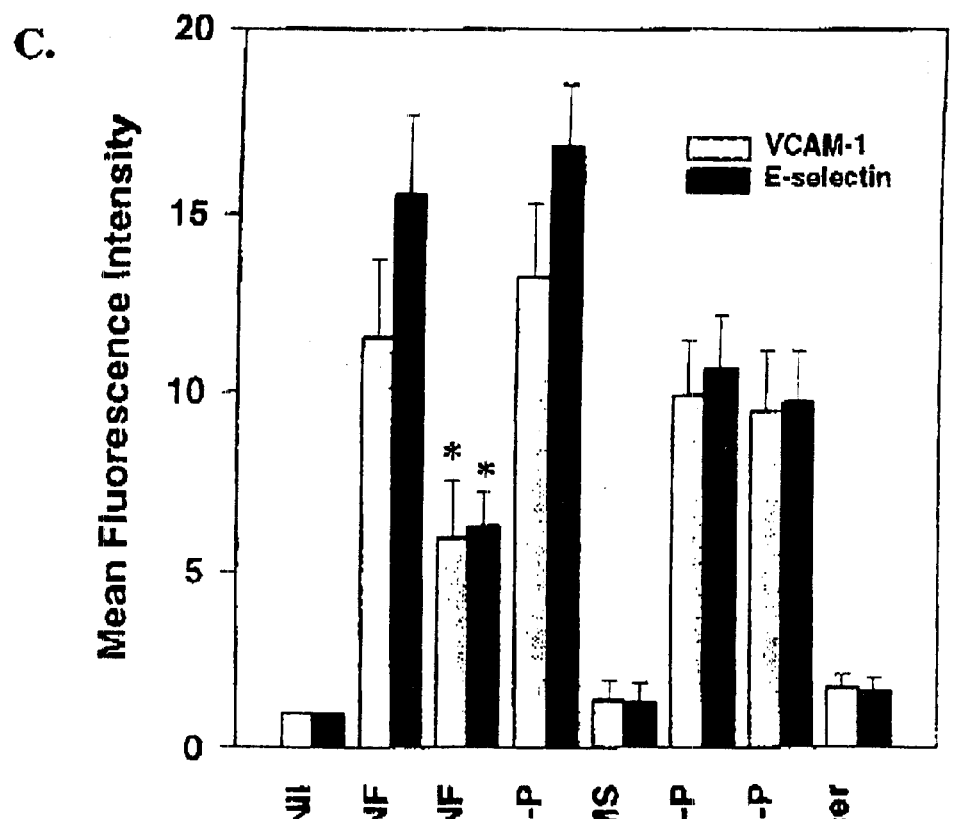
Figure 2:
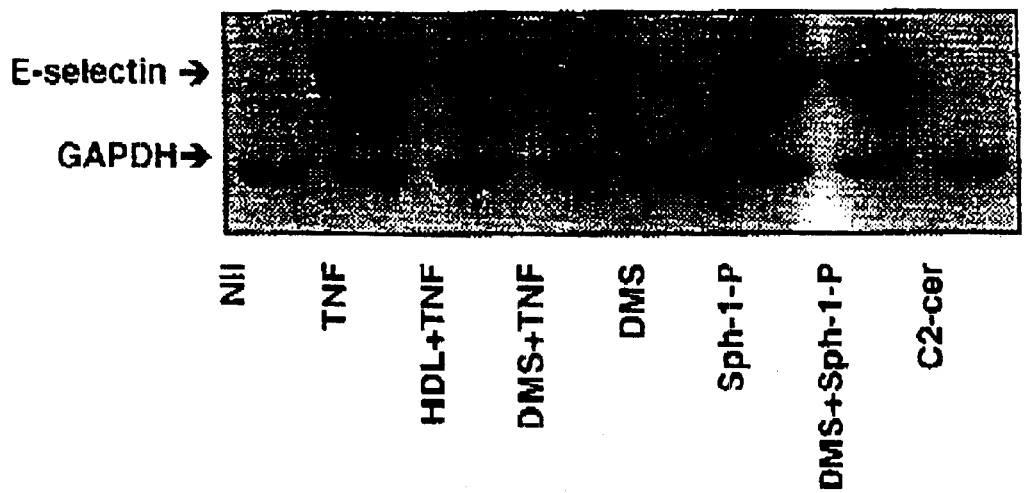

To determine the role of sphingolipid metabolites in adhesion protein expression, either a cell-permeable form of ceramide ($C_2$-ceramide) or sphingomyelinase that generates endogenous ceramide, or Sph-1-P were added to endothelial cells. $C_2$-ceramide (FIG. 2A) or sphingomyelinase were poor stimulators of E-selectin and VCAM-1 expression, reaching levels that were less than 10% of that stimulated by TNF-α. By contrast Sph-1-P was a potent and dose-dependent inducer of E-selectin and VCAM1, reaching levels at 5 $\mu$M that were approximately equivalent to 100 U/ml TNF-α (FIG. 2B). The potency of Sph-1-P was further shown by its induction of E-selectin mRNA (FIG. 2D). To examine the role of Sph-1-P was inhibited by the competitive inhibitor of sphingosine kinase, N,N-dimethylsphingosine (DMS). DMS decreased the TNF-α-induced adhesion protein expression and mRNA levels by between 50 and 70% (FIGS. 2C and D). This demonstrates that sphingose kinase activation is an important event in the TNF-α action. As a control, the same concentration of DMS inhibited sphingosine kinase activity and Sph-1-P formation by >90% induced either by TNF-α or PMA in endothelial cells, PMA has been shown to activate sphingosine kinase via protein kinase C activation (7). In contrast to its effect on TNF-α DMS did not prevent Sph-1-P induced adhesion protein expression (FIG. 2C), indicating a specific effect of DMS on the generation of Sph-1-P. These results show a new signalling pathway for TNF-α-induced adhesion molecule expression. Exogenous cell-permeable ceramide was a potent inhibitor (by >60%) of TNF-α induced adhesion protein expression (FIG. 2A).

EXAMPLE 4

HDL Inhibition of Sphingosine Kinase Signalling

Figure 3:
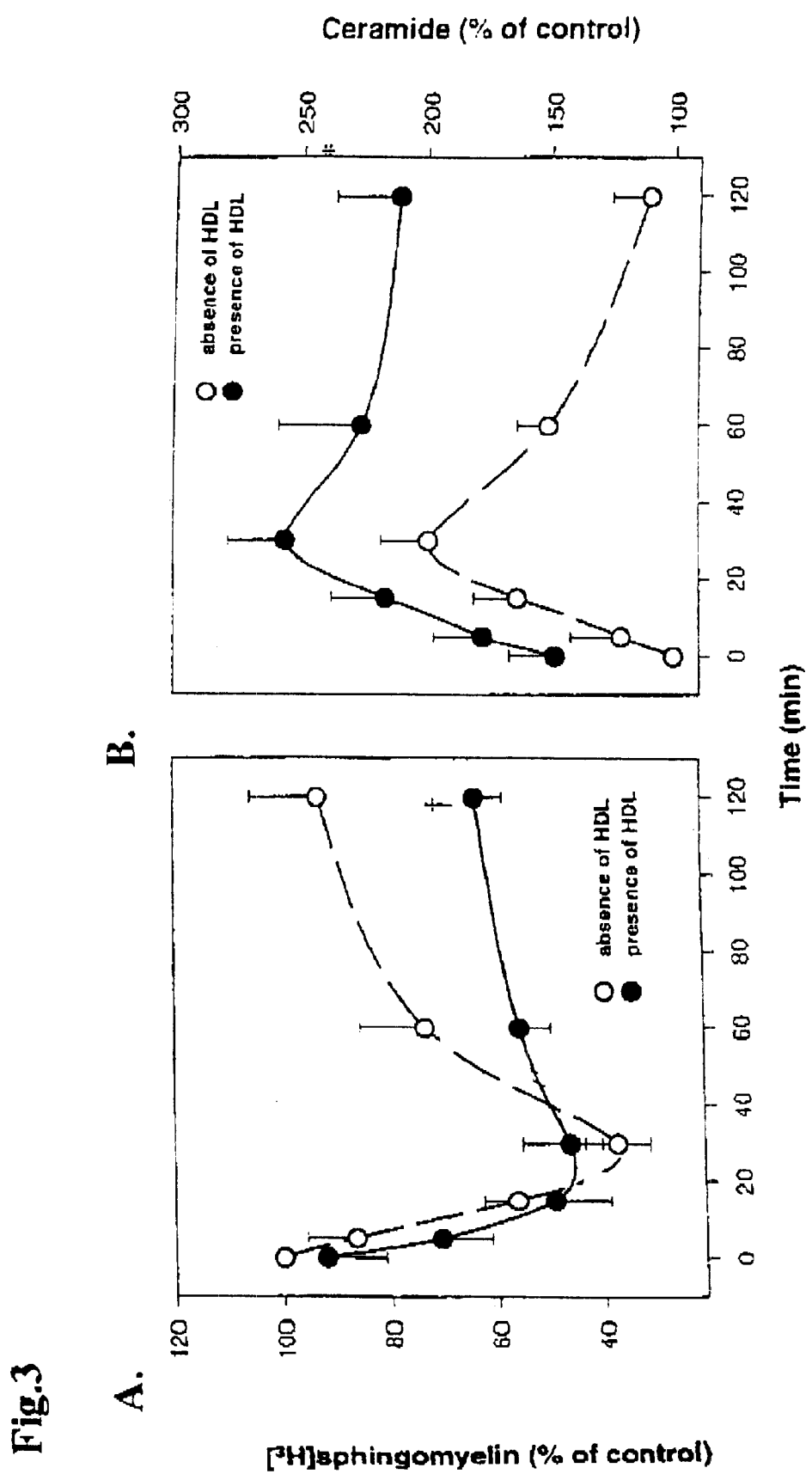
FIG. 3 is a graphical representation of the time course of changes after TNF treatment of HUVECs on key components of sphingomyelin pathway are shown. Open symbols in FIG. 3A show hydrolysis of sphingomyelin in FIG. 3B generation of ceramide, in FIG. 3C sphingosine kinase activity and in FIG. 3D formation of sphingosine-1-phosphate, all as percent of amount at time 0. Filled circles represent the effect of pre-treatment of HUVECs with HDL.
Figure 3:
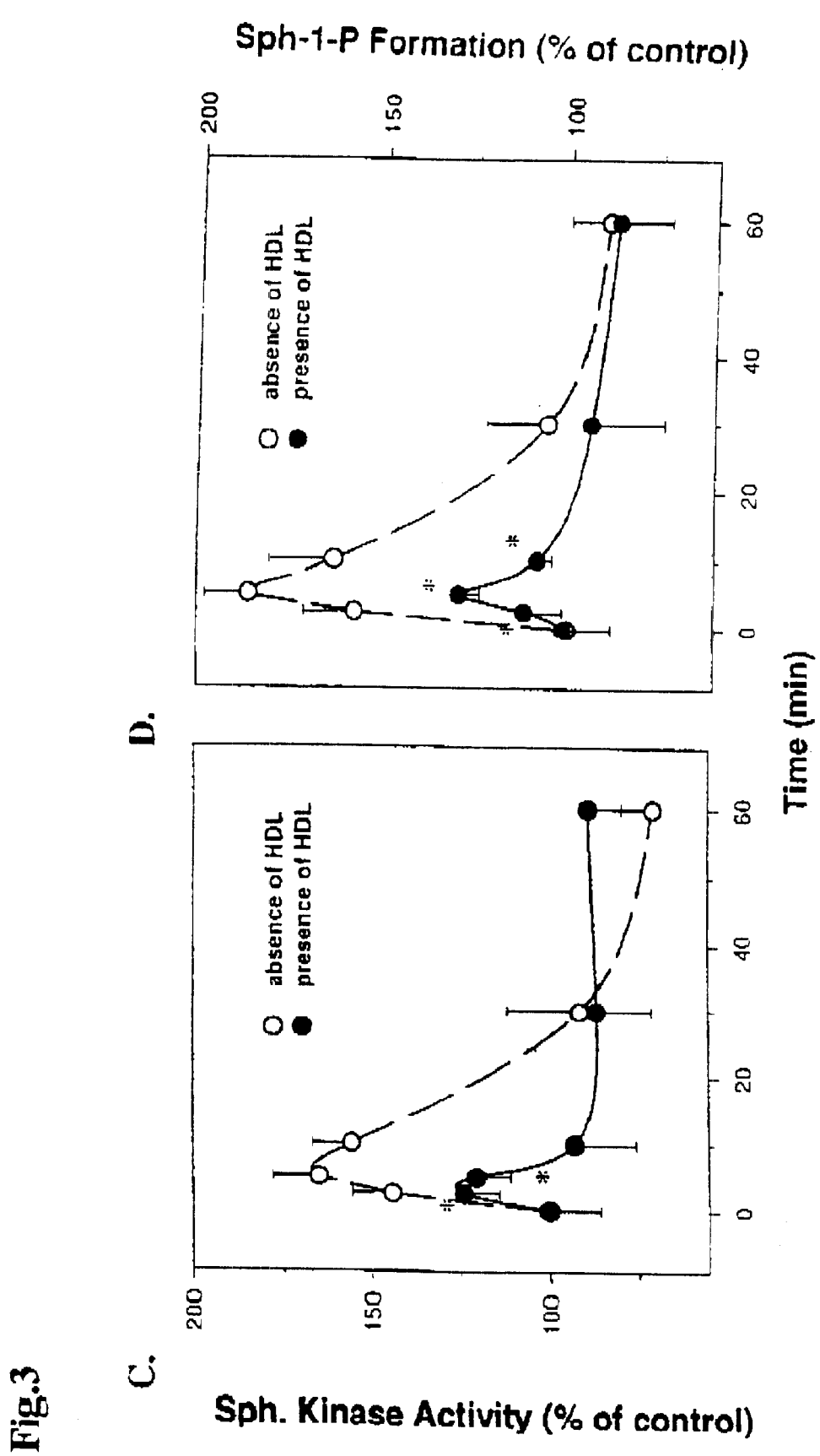

FIG. 3A shows that TNFα stimulation of HUVECs rapidly reduced cellular sphingomyelin content to 40% of control within 30 min with return to near basal levels by 2 h. In parallel, the cellular ceramide levels were rapidly increased (approximately 2 fold) peaking at 30 min after TNFα treatment (FIG. 3B). Treatment of endothelial cells with HDL had a potent effect: it delayed the reversion of post TNFα sphingomyelin levels to base line and sustained the increased ceramide levels after TNFα stimulation.

TNFα stimulation of HUVECs caused a rapid and transient increase in cytosolic sphingosine kinase activity, reaching a maximum of 165±13% (p<0.01) of basal within 5 min. HDL pretreatment profoundly inhibited both the amplitude and duration of TNFα-induced sphingosine kinase activation (FIG. 3C). The production of Sph-1-P was induced in parallel with the sphingosine kinase activity. HDL treatment again substantially blunted the amplitude and duration of Sph-1-P formation (FIG. 3D)

EXAMPLE 5

HDL Inhibition of ERK Cascade

FIG. 4A shows that both TNFα and Sph-1-P were approximately equipment in stimulating ERK activities, whereas $C_2$-ceramide did not. Treatment with DMS inhibited TNFα-activated ERK by 50% (p<0.02), showing a role for sphingosine kinase in the TNFα-activated ERK signal cascade. Preincubation of HUVECs with HDL also reduced TNFα-stimulated ERK activation, consistent with its effect on reducing cellular levels of Sph-1-P (FIG. 4A, bar 4).

EXAMPLE 6

HDL Inhibition of NF-κB Activation

Figure 4:
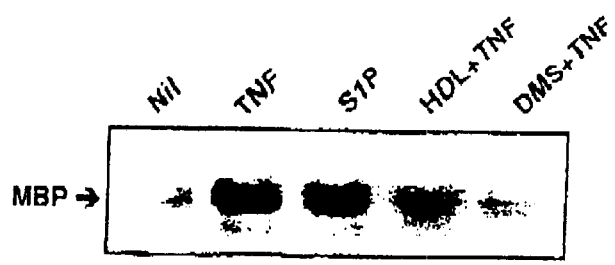
FIG. 4 is a photographic representation of the effect of Sph-1-P, TNF and HDL on generation of ERK (FIG. 4A) and NF-κB (FIG. 4B). The bar graph provides a summary of three independent experiments on ERK activation (±1 SEM). * show p value of difference from TNF by <0.01 and † by <0.05, ‡ shows p<0.01 versus nil counted.
Figure 4:
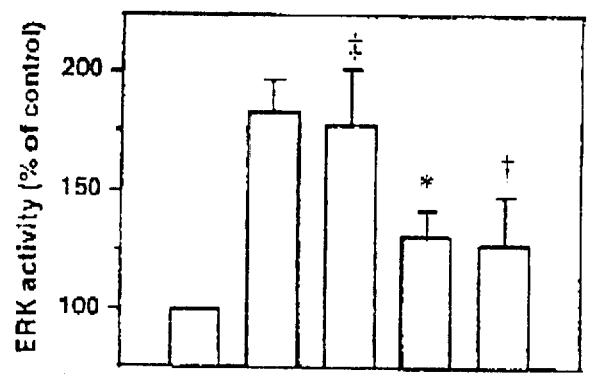
Figure 4:
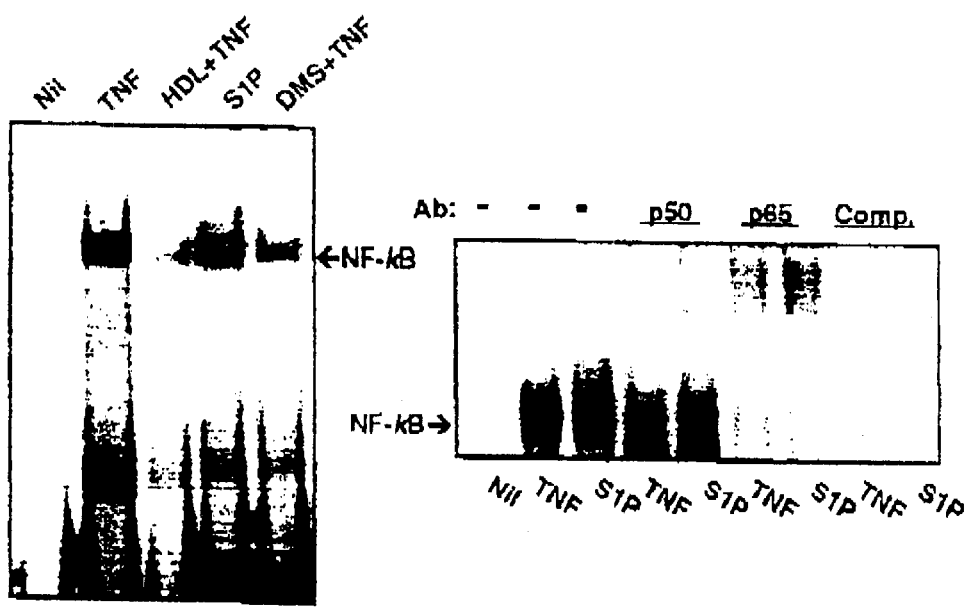
Figure 5:
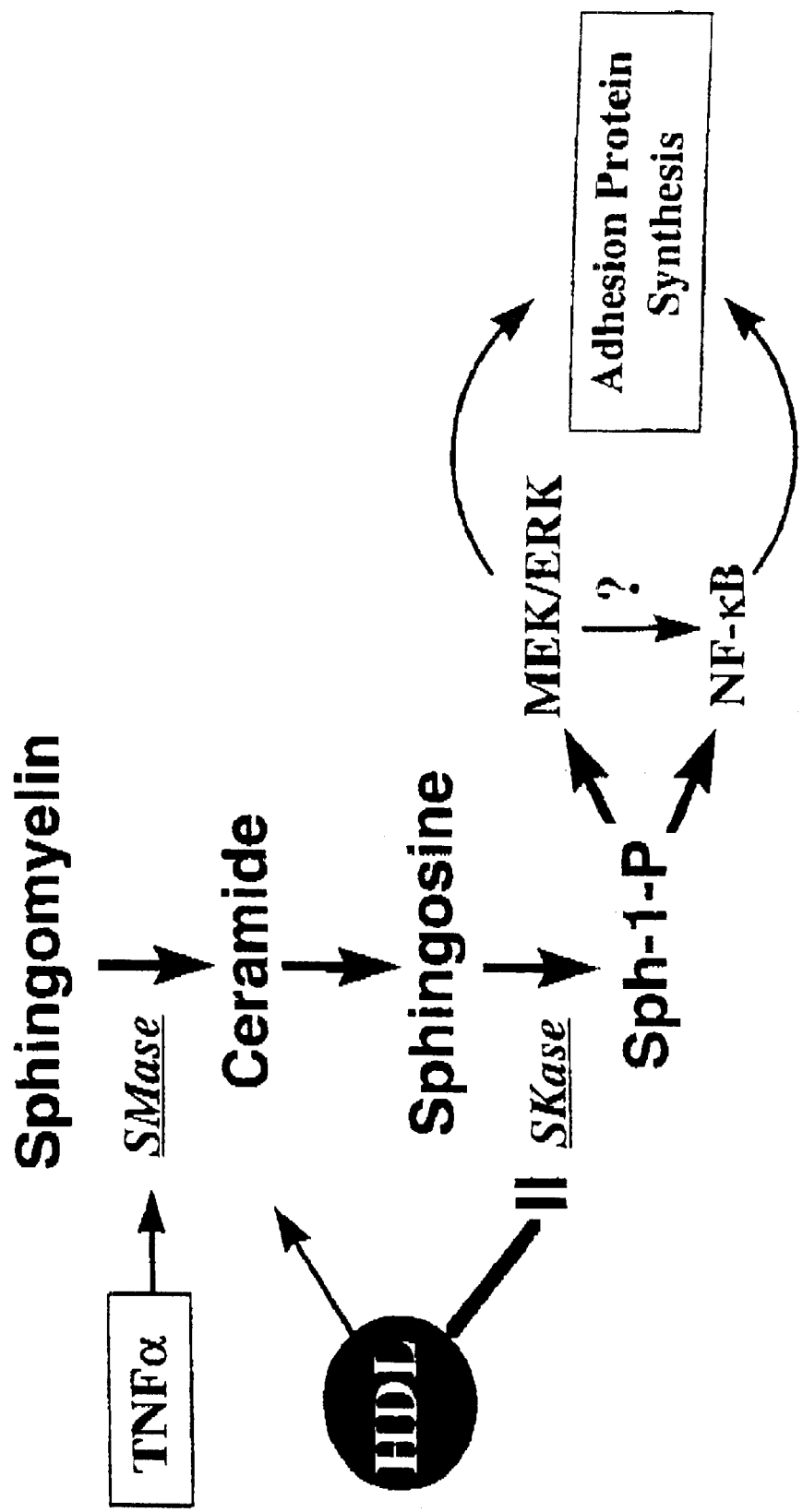
FIG. 5 is a schematic representation of the sphingosine kinase pathway by which HDL inhibits TNFα-induced adhesion protein expression.
Figure 6:
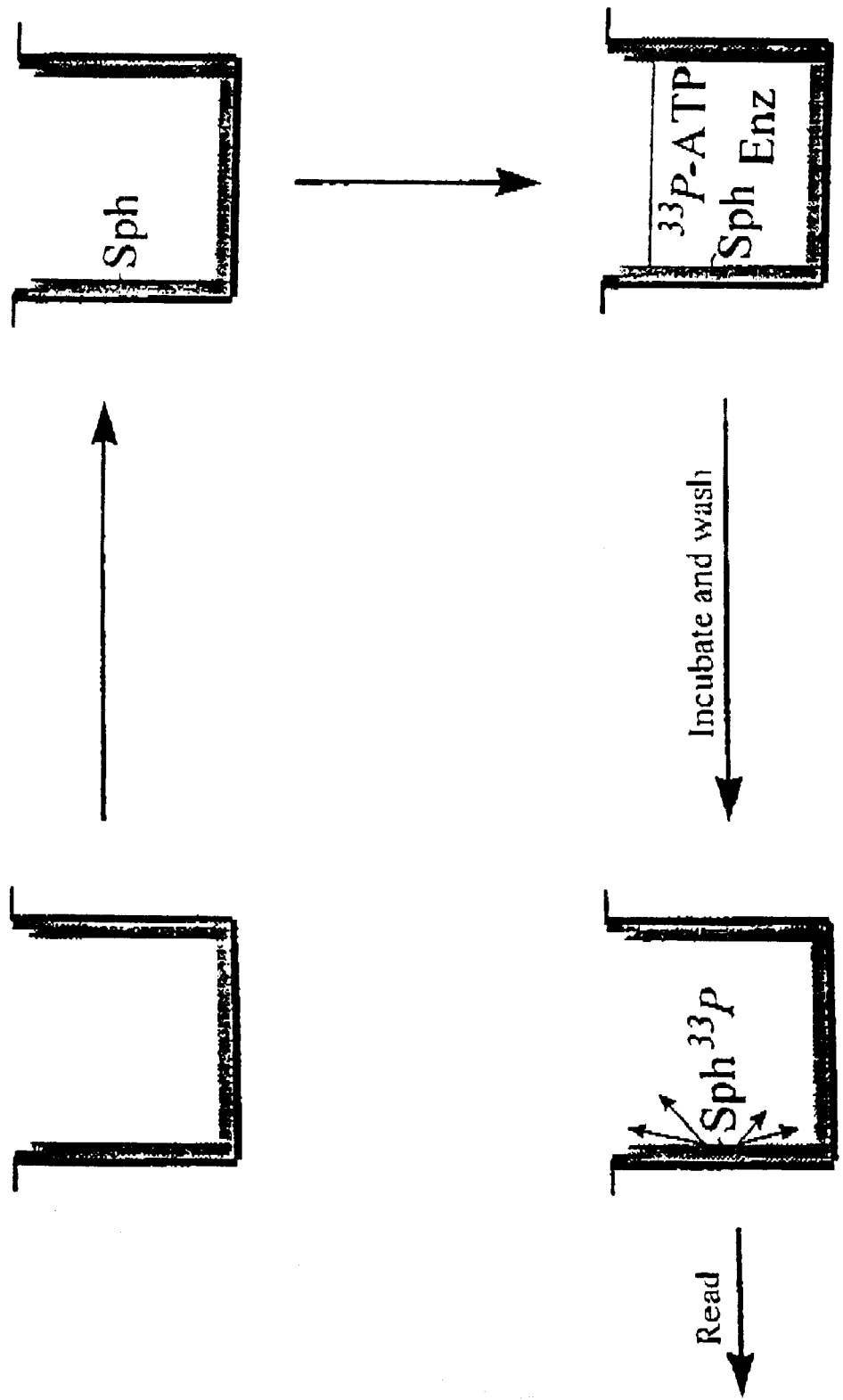
FIG. 6 is a schematic representation of the multi-well assay for sphingosine-kinase activity. The basis of the assay is the phosphorylation of sphingosine bound by absorption to the walls of a multi-well plate in which the walls have been impregnated with scintillant (Flashplates, New England Nuclear). γ-$^{33}$P labelled ATP is incubated in the presence of the source of enzyme. If active enzyme is present the $^{33}$P is transferred to the sphingosine. The wells are then washed to remove unbound $^{33}$P. The $^{33}$P bound to the sphingosine excites the scintillant and a signal is produced that is measured in a scintillation counter.

To measure the NF-κB binding activity, electrophoretic mobility-shift assays were performed. Nuclear extracts were prepared from HUVECs treated for 30 min with vehicle or the indicated agents. The double-stranded oligonucleotides used as a probe in these experiments included 5'-GGATGCCATTGGGGATTTCCTCTTTACTGGATGT-3' (SEQ ID NO: 1) which contains a consensus NF-κB binding site in E-selection promoter that is underlined. Gel mobility shift of a consensus NF-κB oligonucleotide was performed by incubating a $^{32}$P-labelled NF-κB probe with 4 mg of nuclear proteins. The Sph-1-P induced formation of NF-κB specific complexes were similar us that induced by TNFα. These specific DNA-protein complexes were completely abolished by addition of a 50-fold molar excess of unlabeled E-selectin NF-κB oligonucleotides. The specificity of NF-κB binding complex was further identified by the super-shift analyses. Anti-p50 and Anti-p65 polyclonal antibodies (purchased from Santa Cruz Biotechnology. Calif.) were added prior to addition of radiolabeled NF-κB probe. The same phenotype of gel retardation was shown in the gel shift assay after the the preincubation of nuclear extracts from both Sph-1-P and TNFα-treated cells with the antibodies. Electrophoretic mobility shift assay shows that treatment of HUVECs with Sph-1-P induced a significant nuclear NF-κB accumulation (FIG. 4). The composition of Sph-1-P induced NF-κB specific protein-DNA complexes were identical to that induced by TNFα which was revealed to be p50/p65 heterodimer by antibody supershift assay and by competition analyses (FIG. 4B, the bottom). Treatment of cells with HDL or DMS markedly inhibited the TNFα-induced activation of NF-κB by 45–60%. but did not inhibit that induced by Sph-1-P.

EXAMPLE 7

RNA Preparation

Total RNA was prepared from HUVECs that was treated with the indicated agents for 4 h. Equal aliquots of total RNA (12 $\mu$g) were electrophoresed in a 1% formaldehyde gel and transferred to nylon membrane. The blots were hybridized with α$^{32}$P-labeled E-selection cDNA probe. The mRNA levels of E-selectin were quantified by Phosphoimager and normalised to radiolabeled GAPDH probe.

EXAMPLE 8

Spingomyelin Measurement

To measure sphingomyelin, the HUVECs were labeled with [3H]serine (5 $\mu$Ci/ml) for 48 h and preincubated with or without HDL for another 6 h. The cells were then washed three times and incubated for additional 2 h in the presence or absence of HDL. After the treatment with TNFα for the indicated times, cellular lipids were extracted and resolved by thin-layer chromatography (TLC) with chloroform:methanol:acetic acid:water (50:30:8:5, v/v). Sphingomyelin spots were visualized by fluorography, quantitated by scintillation spectrometry, and normalized by radioactivity recovered in total cellular lipids. In the uptake of [$^3$H]serine there are no significant differences between the cells that were preincubated with HDL and with HDL. To measure ceramide levels, cellular ceramide was extracted and quantified with the diacylglycerol kinase reaction (Kolesnick, 1991; Hannun & Bell. 1993) Sphingosine kinase activity was measured in vitro as previously described with some modification (Mattie et al., 1994; Ghosh et al, 1994; Choi et al., 1996). Cells were lysed by passing through 26½ G syringe 6 times in 0.1M HEPES buffer (pH 7.2) containing 10 mM $MgCl_2$, 20% glycerol, 1 mM mecaptoethanol. 1 mM EDTA, 20 μM $ZnCl_2$, 1 mM $Na_3VO_4$, 15 mM NaF, 10 μg/ml leupeptin and aprotinin, 1 mM PMSF and 0.5 mM 4-deoxypyridoxine, Cytosolic fractions were prepared by ultracentrifugation at 105,000×g for 90 min. Sphingosine kinase activity was measured by incubating the supernatant with 20 mM sphingosine-BSA complex and [$\gamma^{32}$P]ATP (1 mM, 5 μCi/ml) for 15 min at 37° C. Labeled lipids were extracted and separated by TLC along with Sph-1-P standard. Radioactivity of the spot corresponding to Sph-1-P was quantified using Phosphoimager system. The measurement of Sph-1-P formation in vivo was performed as previously described (Olivier. 1996). The cells were permeubilized for 15 min at 37° C. in hypotonic buffer (25 mM HEPES. 5 mM $MgCl_2$, 20 μM $Na_3VO_4$, 10 μg/ml leupeptin and aprotinin, 1 mM PMSF and 0.5 mM 4-deoxypyridoxine, pH 7.2) with sphingosine (10 μM) and [$\gamma^{32}$P]ATP (1 μM, 10 μCi/ml). Lipids were extracted and resolved by TLC, and [$\gamma^{32}$P]Sph-1-P was quantified as described above.

EXAMPLE 9

A Multi-Well Assay for Sphingosine-Kinase Activity

Flashplates were coated with lipid substrate by adding 200 μl of a mix of phosphatidylcholine (19.5 μg/ml), phosphatidylserine (5.5 μg/ml). and sphingosine (25 μg/ml) in methanol and evaporating at 30° C. under $N_2$ for 3 hours. A source of sphingosine kinase is added in a buffer consisting of 50 mM HEPES pH 7.2/20% glycerol/10 mM $MgCl_1$/1 mM DTT/20 μM $ZnCl_2$/1 mM $Na_3VO_4$/15 mM NaF/0.5 mM 4-deoxypyridoxine along with [$^{32}$P]-γ-ATP (Bresatech, 1 μCi/well/100 μM) and incubated for up to 2 hours at 37° C. The plates are then washed with 400 μl of 50 mM sodium pyrophosphate, 4 times and radioactivity was measured in a scintillation counter (Top count, Packard).

EXAMPLE 10

Preparation of Homogenates of Tissues for Survey of Sphingosine Kinase Activity Tissues were collected from freshly sacrificed animals and rapidly frozen in liquid nitrogen, 2–5 grams of wet tissue were homogenized with a Polytron tissue homogenizer in 2 volumes of 50 mM Tris pH 7.4/20% glycerol/1 mM DTT/1 mM EDTA, containing a protease inhibitor cocktail (Boehringer-Mannheim). The material was subjected to centrifugation at 7500 g for 30 minutes to remove large fragments. The resulting supernants were further centrifuged at high speed (100,000×g for 1 hour) to generate "supernatant" and "pellet" fractions.

EXAMPLE 11

The Multi-Well Assay is Linear over Time and Specific

Figure 7:
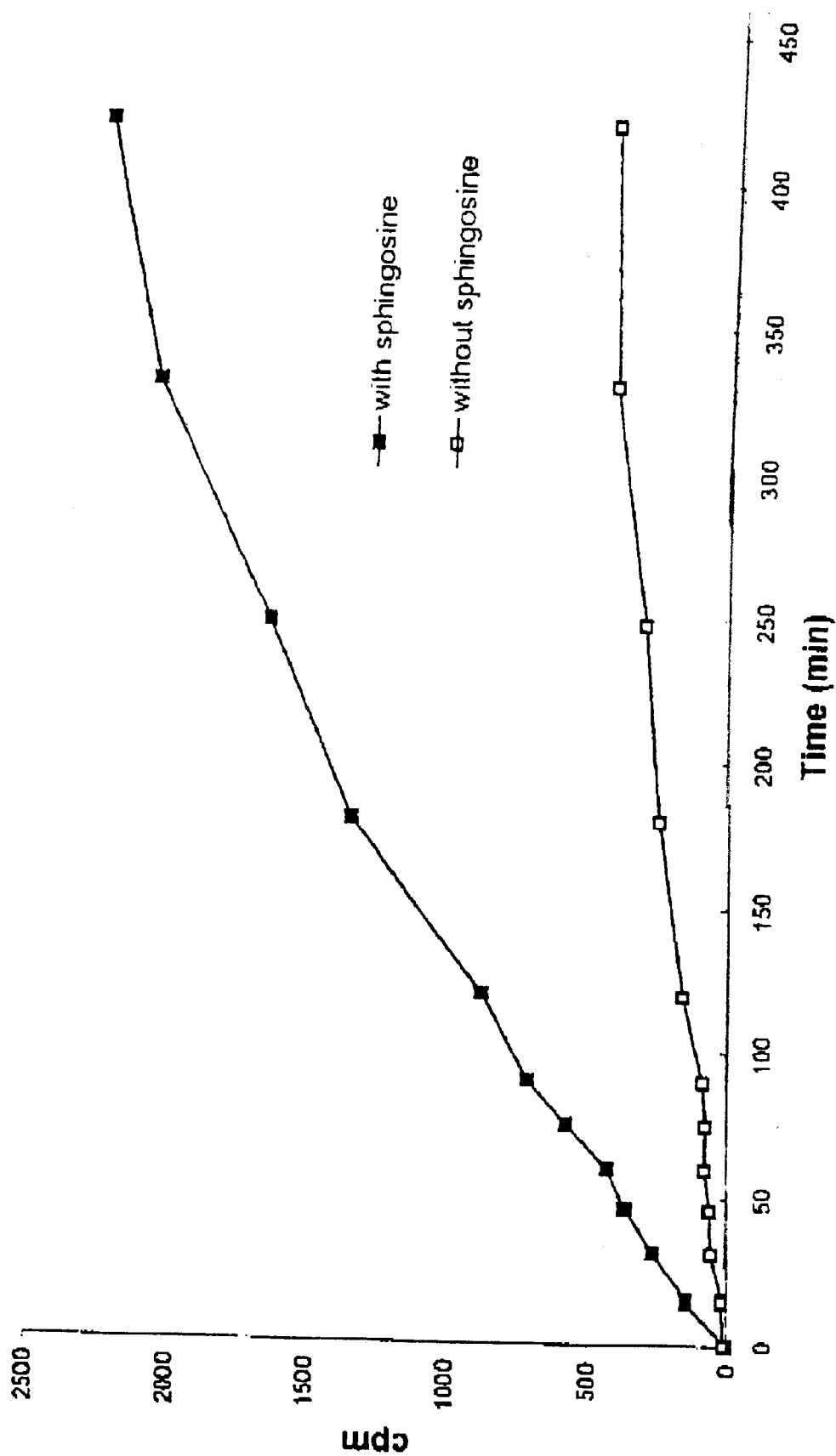
FIG. 7 is a graphical representation showing that sphingosine kinase activity is linear for up to 400 minutes when measured in the multi-well assay. 50 μl of an endothelial cell extract (prepared as described above in example 8, containing sphingosine kinase activity) plus 50 μl of an ATP solution containing 400 μM ATP/20 μCi/ml $^{33}$P-ATP was incubated with flashplates coated with phospholipid mixes either with (filled squares) or without (open squares) sphingosine and incubated at 37° C. for the indicated lengths of time before washing.
Figure 8:
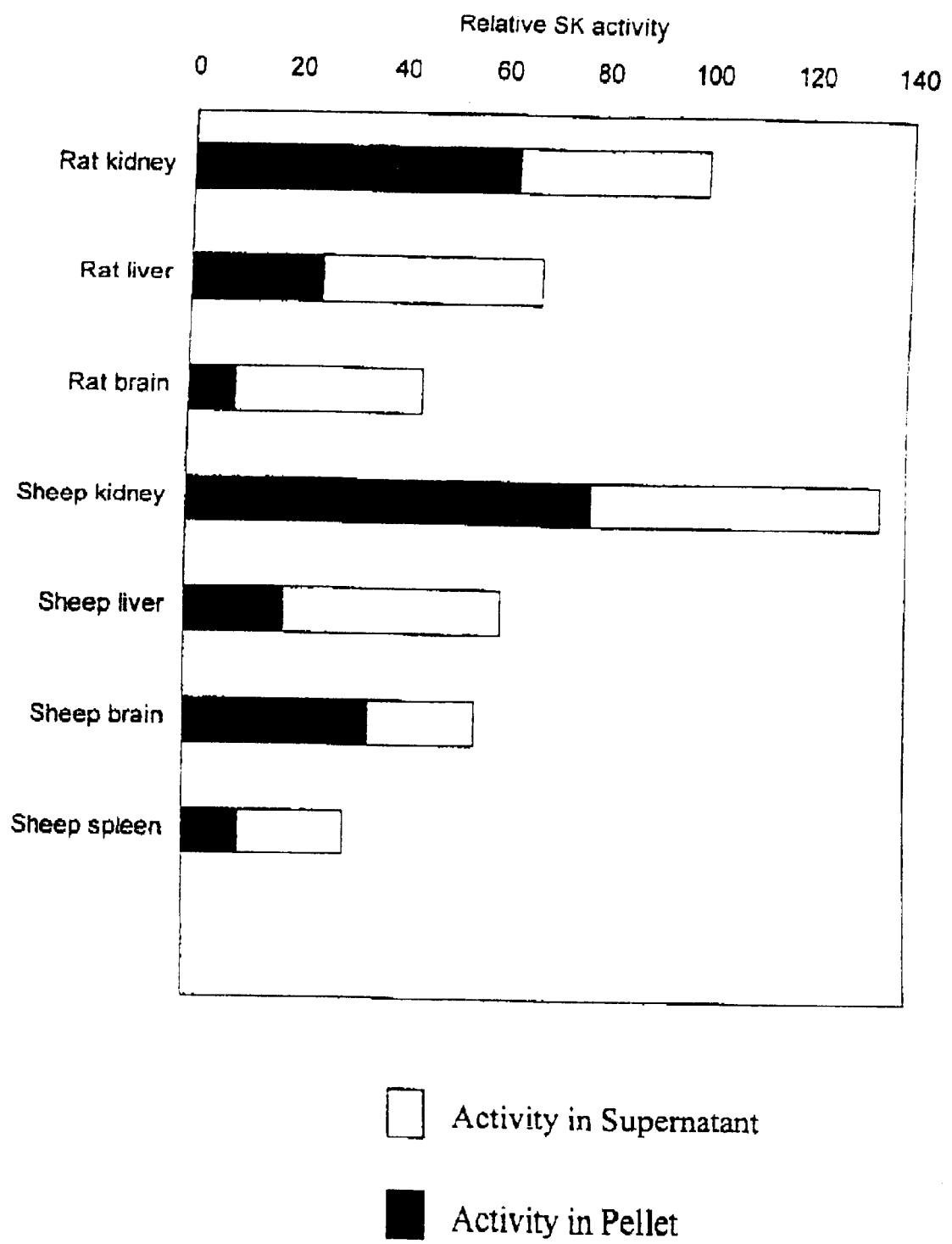
FIG. 8 is a graphical representation of a survey of tissues for sphingosine-kinase activity. High speed "supernatant" (open bar) and "pellet" (filled bar) fractions from 50 μl of extract were then assayed for sphingosine kinase activity.

FIG. 7 illustrates the results of assaying for sphingosine kinase activity from a lysate made from human umbilical endothelial cells. It can be seen that the signal increases linearly over a period of approximately 400 minutes. This signal is specific to sphingosine kinase since omitting sphingosine from the lipid mix used to coat the plates reduces the resulting signal to background levels. This demonstrates that it is sphingosine, and not some other component of the lipid or assay mix, that is being phosphorylated in the assay. This is remarkable since this assay was done with a crude lysate which would be expected to contain a number of lipid and protein kinases.

EXAMPLE 12

Sphingosine-Kinase Agonist and Antagonist Activity Measurement

Plates are prepared as described in Example 9. Sphingosine kinase (prepared in buffer together with $^{33}$P-ATP as described in Example 9) is added in the presence of an agent to be tested for antagonistic or agonistic activity. The agent is added to a level of enzyme activity yielding a linear response with respect to time from 0–3 hours of incubation. Plates are incubated for two hours at 37° C., washed as in Example 9 and phosphorylation of sphingosine is determined by scintillation counting.

Inhibition (antagonistic activity) is detected as diminished incorporation of $^{33}$P and stimulation (agonistic activity) is detected as increased incorporation of $^{33}$P relative to a control incubation containing an equivalent amount of the vehicle solvent used to deliver the agents tested.

Those skilled in the art will appreciate that the invention described herein is susceptible to variations and modifications other than those specifically described. It is to be understood that the invention includes all such variations and modifications which fall within its spirit and scope. The invention also includes all of the steps, features, compositions and compounds referred to or indicated in this specification, individually or collectively, and any and all combinations of any two or more of so steps or features.

BIBLIOGRAPHY

Abbassi O. Kishimoto T. K. McIntire I. V., Anderson D. C., Smith C. W., *J. Clin. Invest.* 92:2719–2730 (1993)
Berra E. et al., *EMBO J.* 14:6157 (1995)
Choi O. H., Kim J. H., Kinet J. P., *Nature* 380:634 (1996)
Ghosh T. K. Bian J., Gill D. L., *J. Biol. Chem.* 269:22628 (1994)
Hannun Y. A., Bell R. M., *Adv. Lipid Res.* 25:27 (1993)
Johnson-Tidey R. R., McGregor J. L., Taylor P. R., Poston R. N., *Am. J. Pathol.* 144:952–961 (1994)
Kolesnick R. N., *Prog. Lipid Res.* 30:1 (1991)
Lee F. S., Hagler J., Chen Z. J., Maniatis T., *Cell* 58:213 (1997)
Li Y. S. et al., *Mol. Cell. Biol.* 16:5947 (1996)
Mattie M., Brooker G., Spiegel S., *J. Biol. Chem.* 269:3181 (1994)
O'Brien K. D. et al., *J. Clin. Invest.* 92:945 (1993)
O'Brien K. D., Allen M. D., McDonald T. O., Chait A., Harlan J. M., Fishbein D., McCarty J., Furgerson M., Hudkins K., Benjamin C. D., Lobb R., Alpers C. R., *J. Clin. Invest.* 92:945–951 (1993)

Olivier C. et al., *Nature* 381:800 (1996)

Van der Wal A. C., Das P. K., Tigges A. J., Becker A. R., *Am. J. Pathol.* 141:161–168 (1992)

Wood K. M., Cadogan M. D., Ranshaw A. I., Parums D. V., *Histopathology* 22;437–444 (1993)

World Health Organization *World Health Statistics Annual.* Geneva, Switzerland (1993)

What is claimed is:

1. A screening method for identifying a therapeutic candidate for a coronary heart disease or an inflammatory condition that comprises
   (i) bringing at least one agent into contact with at least one component of a sphingosine kinase signaling pathway, under conditions such that an effect on the activity of said component is detectable, and
   (ii) detecting the presence or absence of said effect, whereby detecting said effect indicates said agent as a therapeutic candidate with respect to coronary heart disease or an inflammatory condition.

2. The method as claimed in claim 1 wherein said effect results in disrupting the sphingosine kinase signaling pathway thereby inhibiting adhesion molecule expression.

3. The method as claimed in claim 1, wherein said component is selected from the group consisting of sphingosine, sphingosine kinase, and Sph-1-P.

4. The method as claimed in claim 1 wherein said component is Sph-1-P.

5. The method as claimed in claim 1 wherein said component is sphingosine kinase.

6. The method as claimed in claim 1 wherein said effect is inhibition of the activity of Sph-1-P.

7. The method as claimed in claim 1 wherein said effect is inhibition of the activity of sphingosine kinase.

8. A screening method that comprises
   (i) identifying a disease condition in which up-regulation of an adhesion molecule is harmful,
   (ii) providing a solid support to which sphingosine is bound;
   (iii) contacting the solid support with sphingosine kinase and $^{33}$P-ATP in the presence or absence of an agent; and
   (iii) comparing an amount of bound $^{33}$P produced in the presence of said agent with that produced in the absence of said agent, whereby a difference in said amount indicates said agent as a therapeutic candidate with respect to said disease.

* * * * *